United States Patent [19]
Castel

[11] Patent Number: 5,770,805
[45] Date of Patent: Jun. 23, 1998

[54] METHOD AND DEVICE FOR MEASURING A PARAMETER OF A FLUID HAVING VARIABLE DENSITY

[75] Inventor: Yvon Castel, Croissy sur Seine, France

[73] Assignee: Institut Francais du Petrole, Rueil Malmaison, France

[21] Appl. No.: 734,269

[22] Filed: Oct. 21, 1996

[30] Foreign Application Priority Data

Oct. 19, 1995 [FR] France .................................. 95 12422

[51] Int. Cl.[6] ...................................................... G01F 1/74
[52] U.S. Cl. ...................................................... 73/861.04
[58] Field of Search ........................... 73/861.04, 861.21, 73/269, 232, 262, 263

[56] References Cited

U.S. PATENT DOCUMENTS

| 3,130,586 | 4/1964 | Taylor et al. . |
| 4,860,594 | 8/1989 | Hammond et al. . |
| 4,920,794 | 5/1990 | Ingman ................................. 73/861.21 |
| 5,347,862 | 9/1994 | Ingman ................................. 73/861.21 |
| 5,390,542 | 2/1995 | O'Rouke .............................. 73/861.21 |

FOREIGN PATENT DOCUMENTS

| 0206855 | 12/1986 | European Pat. Off. . |
| 0370873 | 5/1990 | European Pat. Off. . |
| 2345716 | 10/1977 | France . |
| 57112525 | 1/1984 | Japan ..................................... 73/269 |
| 901-823 | 1/1982 | U.S.S.R. ............................... 73/269 |

*Primary Examiner*—Richard Chilcot
*Assistant Examiner*—Jewel Artis
*Attorney, Agent, or Firm*—Antonelli, Terry, Stout & Kraus, LLP

[57] ABSTRACT

A device for determining at least one parameter characteristic of a fluid with a variable density and at least one phase having different density values is disclosed. A process of measuring the density of a multi-phase petroleum effluent. A parameter associated with a fluid of variable density is determined by measuring the value by which a flexible element in contact with the fluid is deformed.

15 Claims, 5 Drawing Sheets

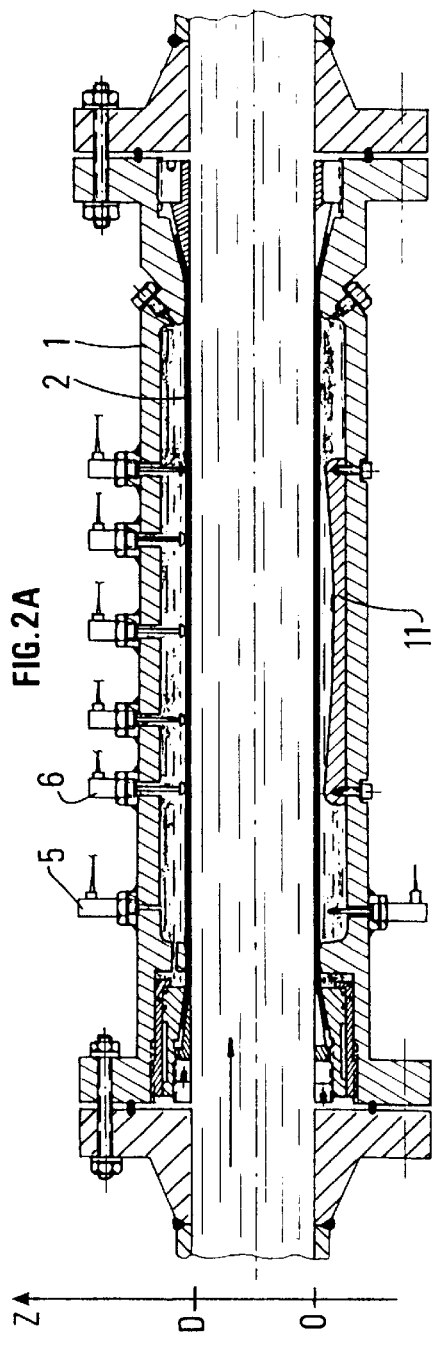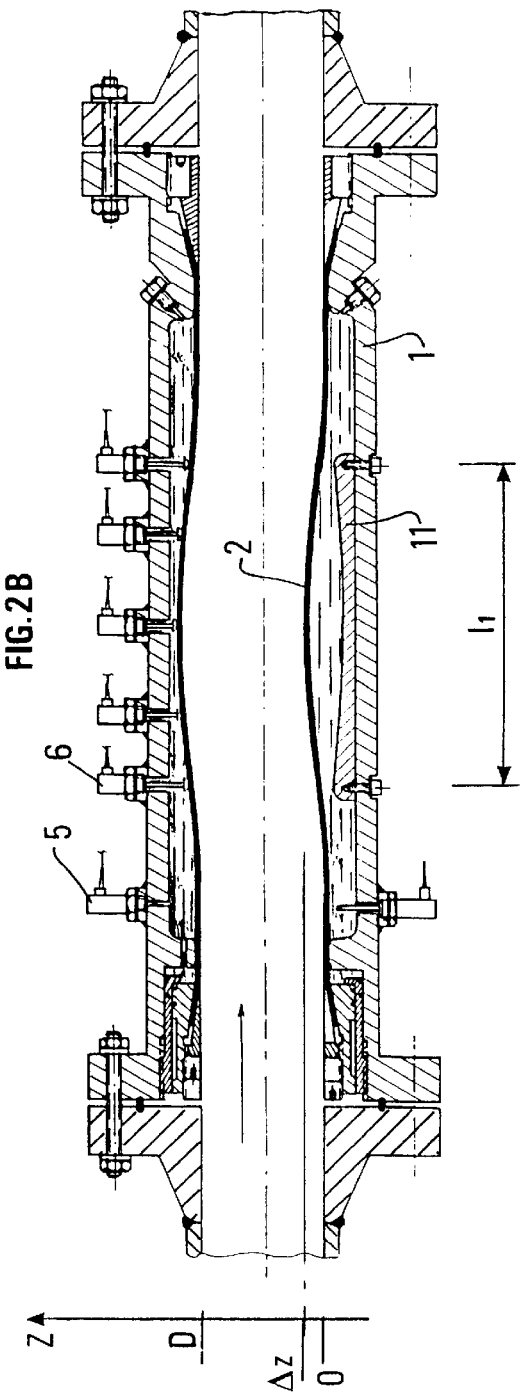

5,770,805

METHOD AND DEVICE FOR MEASURING A PARAMETER OF A FLUID HAVING VARIABLE DENSITY

FIELD OF THE INVENTION

The present invention relates to a device and a method for determining at least one parameter associated with a fluid of variable density using a measurement of the deformation occurring in a flexible element in contact therewith.

The objective of the invention, therefore, is to determine the density of the fluid and/or the quantity of each of the fluid phases and/or the flow rate values of the different phases and/or the fluid. The device of the invention finds its application in numerous fields and in particular in respect of hydrocarbon pumping and pipeline transportation systems.

BACKGROUND OF THE INVENTION

The prior art describes numerous devices enabling the quantities of the phases contained in a multi-phase effluent to be ascertained as well as the flow rate thereof.

Some devices measure the capacitance or conductance of the multi-phase medium. These devices have numerous disadvantages, however, amongst them the conductivity of the medium and leaks between electrodes, and there is also the possibility that a film will build up, forming a wall that will distort the measuring process and reduce the reliability and simplicity of the measurements on an industrial scale.

Other devices make use of gamma or neutron radiation or electromagnetic waves.

A method is also known whereby nuclear magnetic resonance (NMR) is used to measure the proportions and flow rates of the water and oil in the circulating petroleum fluids. Devices based on this principle are generally cumbersome and their response times such that they are incompatible with the constraints inherent in the petroleum industry.

Furthermore, these devices use expensive radiation sources that can be dangerous and require monitoring because of the problems of drift that can occur over time.

Patent FR-2.639.434 filed by the present applicant teaches a method of weighing a pipe of a known volume, through which a composite multi-phase fluid having a variable density is circulated. The presence of successive plugs of liquid and gas or the presence of particles can give rise to vibrations which introduce errors into the measurements.

The principles of volumetric flow measurement using deformations occurring in a metal tube, which may or may not be rectilinear, used alone in larger quantities, subjected to transverse vibrations imposed thereon and reacting by deviations in antinodes by dint of what is known as the Coriolis effect, are not suitable for analyzing fluids that contain a gaseous phase since even a small amount of gas can cause significant distortion of the measurements.

Another measuring method basically consists in measuring the pressure differential between the upper and lower portions of an essentially horizontally positioned pipe. This method is not very well suited to petroleum fluids which may contain solid particles that are likely to block the pressure sampling orifices or to operating methods where the manometer pipes are penetrated by the gas in the event of rapid pressure loss in the main pipe. Furthermore, their response time is often too long.

SUMMARY OF THE INVENTION

The purpose of the invention is to overcome the specific drawbacks listed above and relates to a device and a method for determining the composition of a fluid and measuring flow rates, which precludes any risks to the environment either onshore or offshore.

An advantage of the device is that it can be incorporated in an effluent transport system in the form of a sleeve which is inserted between the pipe elements. It is easy to manufacture and can be readily adapted to cater for any diameter and any working pressure.

Furthermore, the device is based on reliable and simple mechanical means of passive measurement, and is therefore not expensive.

BRIEF DESCRIPTION OF THE FIGURES

FIGS. 2A, 2B are diagrams showing deformation of the membrane caused by the flow effect.

DESCRIPTION OF THE PREFERRED EMBODIMENTS

Figure 1:
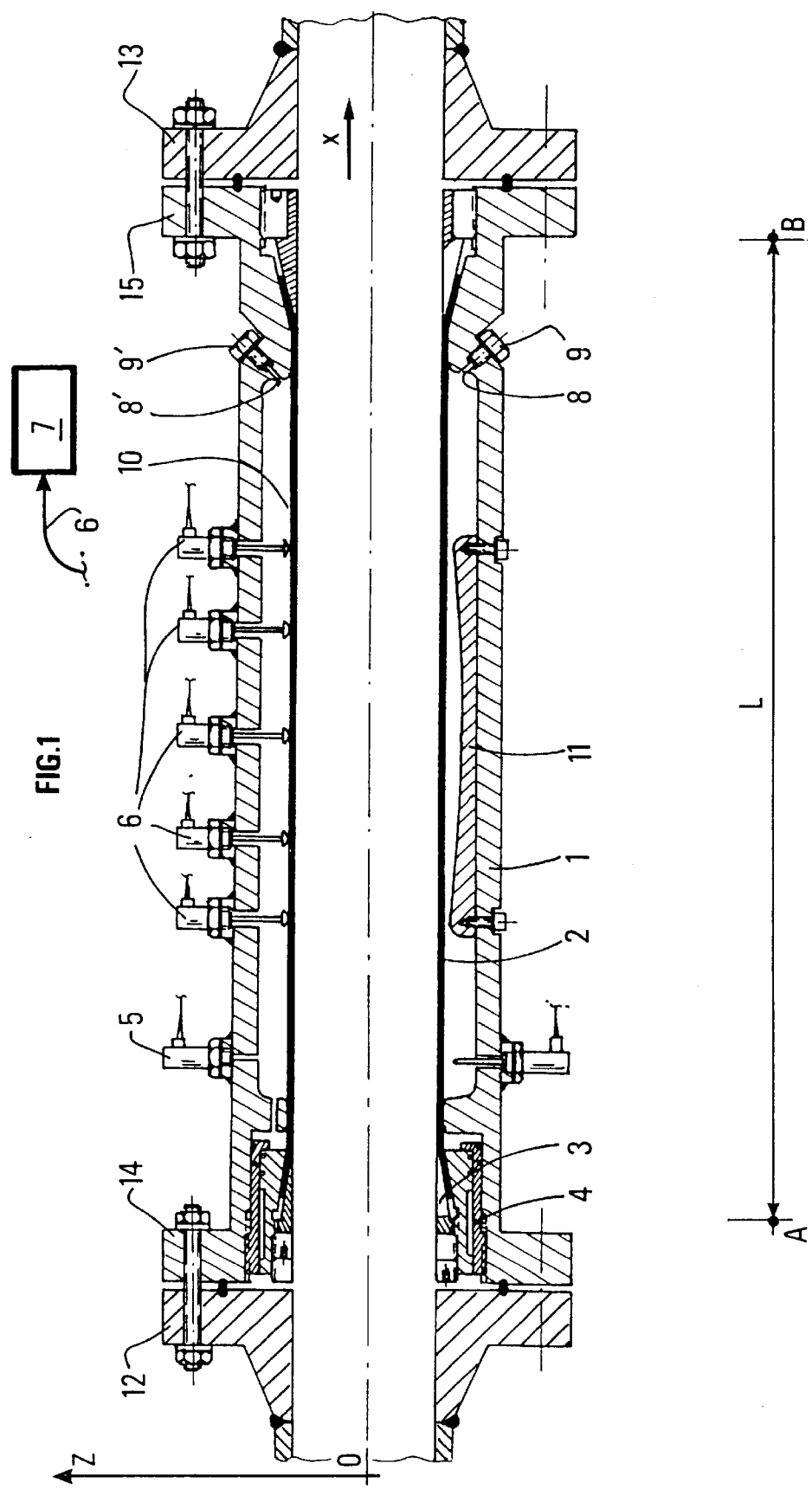
FIG. 1 shows an example of an embodiment of the device of the invention.

Throughout the following description, the term "deformation" is used to denote the deformation in the membrane or flexible element relative to a reference value and obtained under the effect of a fluid whose density or specific mass varies. The deformation of the membrane specifically corresponds to a curve representing the shape assumed by a generatrix of the membrane.

The purpose of the method of the invention is to determine at least one parameter associated with a fluid which has a variable specific mass or density, where the fluid may contain one or several phases whose densities may vary.

The method of the invention is characterised in that a measurement is taken of the deformation of a flexible element, such as a membrane, in contact with the fluid at several points distributed over at least a part of its length, the flexible element being at equi-pressure and fixed to the pipe, for example, at two points at least, and these measurements are used in conjunction with a relationship linking the measurements, and/or the curve passing through these various plotted measurements, and/or the slope of the curve, to determine at least one parameter characterizing the said fluid, such as its average density, and/or the density of each of its phases, and/or the quantity of each of its phases and/or the variation in its composition.

It is to advantage to take measurements of the deformation value at several points distributed over at least a length of the flexible element and these measurements are used in conjunction with a relationship which links them and/or the curve passing through these various plotted measurements and/or the slope of the curve to determine at least one of the said parameters characterising the fluid. The length of the flexible element is a generatrix of the flexible element, for example.

Advantageously, the deformation of the said flexible element is measured at a point located at a distance of essentially 0.2*L from one of the fixing points, L being the total length of the flexible element.

The fluid can be passed through a pipe fitted with a deformable, flexible element, and the speed of at least one of the phases of the fluid determined and these deformation measurements and the speed value used to derive the average flow rate value and/or the flow rate of each of the phases in the fluid.

Two deformation measurements are taken at two successive instants, for example, and the two measurements are correlated to derive the speed associated with at least one of the fluid phases.

The present invention also relates to a device for determining at least one parameter characteristic of a fluid which has a variable density, the said fluid possibly containing one or several phases of different density values. The device is characterized in that it has an enclosure comprising at least one flexible element capable of deformation in contact with the fluid, the said flexible element being fixed at two points (A, B) to a wall of the enclosure, the said flexible element being so arranged in relation to the internal wall of the said enclosure that an annular space is created and the enclosure is provided, for example, with means for introducing at least one auxiliary, non-compressible fluid into the said annular space to place the said element at equi-pressure, at least one means for measuring the deformation of the said flexible element in contact with the fluid, a suitable processing device connected to the measuring means, for example, so that these measured values can be used to calculate the said parameter, which might be its variation and/or the quantity of each of the phases and/or the speed of each of the phases and/or the structure of the said fluid and/or its average density and/or the density of each of its phases and/or the variation in its composition.

The measuring means may be sensors, such as: a mechanical, inductive or capacitive sensor, the axis of the sensors forming an angle of between −15 and +15° relative to the longitudinal axis of the pipe.

The flexible element is a membrane, for example, provided with stiffening members enabling a friction measurement to be taken.

By preference, the device is used in a substantially horizontal position between two pieces of a same pipe.

The method and device of the invention are particularly well suited for determining the variation in structure and/or the quantity of at least one of the phases of a fluid and/or the flow rate of each of the phases of a multi-phase fluid and/or a two-phase petroleum effluent having at least one liquid phase such as water and/or oil and at least one gaseous phase.

The invention can be applied in particular to fluids of variable density, such as multi-phase fluids comprising one or several phases, circulating in a pipe.

The method and device of the invention are especially suitable for two-phase fluids made up of at least a liquid phase and a gaseous phase.

Another specific application of the method and device of the present invention is that of transporting fluids containing solid substances suspended in a liquid, such as coal, gravel, clinker cement, concrete or drilling muds.

The present invention can also be used to analyse fluids that are homogenous to a greater or lesser degree, such as drilling muds, brine used for leaching subterranean cavities or various industrial mixtures.

The invention can be applied to advantage in the petroleum industry for determining at least one parameter relating to a multi-phase effluent, which might be of various forms or flow types, most frequently in plugs or stratified flows.

It is necessary to have a knowledge of the proportions of each of the phases, for example, and an accurate knowledge of their flow rates measured simultaneously at the production well output, in order to monitor and ensure the production safety of each well. These data help to improve production monitoring and protect the network of flowlines conveying the crude effluent to a processing centre and also optimise operation of pumping devices used to transport the effluents where the phases are not separated as well as equipment at the processing centre which has to be preset.

In particular, a knowledge of these data can be used to:

provide the base data for the programs simulating the behaviour of the multi-phase flows in the flowline or despatching networks, when positioned upstream of the equipment, anticipate the arrival, volume and speed of liquid and/or gas plugs in the equipment linked to the production unit such as the pumps or separators so that they can be configured to take account of the flow type.

It is also possible to determine the flow profiles of a multi-phase effluent circulating in a substantially horizontal pipe, especially what are known as stratified profiles and the profiles of liquid plugs, which is the case in about 90% of two-phase petroleum production.

The present invention can also be applied in other fields, for example to control two-phase flows in the nuclear industry and the chemical and petrol refining industries, or for single-phase fluids of variable density.

In particular, the device and method of the invention make it possible to handle the pressure level, measure the displacement speed of heads and/or tails of liquid plugs, adapt to all pipe dimensions in which the two-phase effluent might be circulated, reduce susceptibility to abrasion due to any solid particles present in the multi-phase fluid and in particular allow a passage for devices used in the petroleum industry, such as scrapers, due to the fact that the element used to measure deformation is flexible.

In the case of fluids in which the density is variable, such as drilling muds, the present invention has the advantage of being robust and reliable, especially with fluids which are abrasive in nature.

Other features and advantages of the method and device of the invention will become clear from the examples of embodiments described below in the context of applications, which are in no respect limiting, relating to a multi-phase petroleum fluid flowing in a pipe and with reference to the appended drawings.

The principle of the invention is to measure the deformation at one or several points of a flexible element, such as a membrane, in contact with a fluid of variable density, where the fluid is in a state of flow.

The membrane can be likened to a deformable beam which deflects to varying degrees depending on the load, the shape assumed by the membrane being essentially attributable to the distribution of loads with which it is in contact.

One or several deflection measurements are used to determine at least one parameter associated with the fluid, such as its average density, or the proportion of each of the phases in a multi-phase fluid containing phases of varying density values so that the different degrees to which they deform the membrane can be ascertained.

The deflection is the measurement of the membrane displacement or deformation at a given point of the membrane referred to an initial state.

In the case of a fluid flowing through a pipe, several measurement points can be correlated to determine the speed of the fluid and/or each of the phases in a multi-phase fluid, for example, and its flow rate or the flow rate of each of the phases is calculated.

By preference, the device of the invention is placed in a substantially horizontal position or a position such that the angle formed by the axis of the pipe with the horizontal is small.

FIG. 1 shows a device used in the context of petroleum production, for example.

It consists of a measuring sleeve that is inserted between two elements of a pipe 12, 13, in which a multi-phase fluid is circulating. This sleeve comprises a rigid tube 1 provided at each of its opposite ends with fixing straps 14, 15 so that it can be attached to the portions of the pipe.

A flexible element or deformable membrane 2, preferably of a shape that matches that of the tube 1, is arranged on the inside and joined to the latter by fixing means 3. The mounting of the two ends of the membrane 2 is a sealed mounting assembly (planes A and B of FIG. 1). The mounting assembly upstream of the membrane in particular, illustrated in the drawing by the plane A, which meets the head of the flow, is deigned to withstand the pressure of the fluid flow as it penetrates the pipe. In the case of a circular geometry, the diameter d of the membrane 2 is smaller than the diameter of the tube 1.

Advantageously, the membrane 2 is fixed and stretched by means of tightening elements 4, providing the option of regulating the tension so as to optimize the measurements.

The flexible membrane 2 is preferably made from a material of the elastomer type, capable of withstanding chemical attack and abrasion by the fluids contained in the enclosure, particularly petroleum effluents that are likely to contain acid gases and solid particles.

In the case of applications where the curvature of the membrane is large, materials of adequate stiffness are used that are capable of withstanding deformation and at the same time of giving true and accurate deformation measurements.

Various examples of embodiments of the membrane are given by way of illustration, but are not restrictive, in FIGS. 5A to 5D.

The measuring sleeve may incorporate a pressure sensor 5 located at its inlet, for example, which corresponds to the side at which the effluent arrives (point A in FIG. 1) or the upstream side.

The pressure sensor 5 is a submersible, explosion-proof sensor, for example, protected by the membrane and provides a means of minimizing the risk of the pressure sampling process from being distorted by clogging due to solid particles entrained with the effluent.

One or several sensors 6 are used to measure the position of the flexible membrane 2 as a means of ascertaining the deflection value of the membrane due to the deformation thereof.

These sensors are of the mechanical type, for example, with followers in contact with the flexible membrane. This being the case, the deformation measurement of the membrane is taken with reference to an initial idle position of the flexible membrane, for example, located on an axis Oz essentially perpendicular to the longitudinal axis X of the sleeve (FIG. 2A).

The sensor may be a sensor of the potentiometer type with mutual induction and extensometer gauges, for example, or an accelerometer.

The sensor 6 measuring the deformation may also be a no-contact sensor, such as an inductive or capacitive sensor, a laser and fiber glass sensor offering a high degree of intrinsic safety, or an ultra-sound sensor.

The number and distribution of position sensors 6 is selected to suit the required result and the method to suit the data processing requirements.

Advantageously, they are distributed along a same generatrix of the flexible membrane, on the lower portion and/or on the upper portion thereof. For example, if a petroleum fluid is flowing in a pipe, the sensors are able to monitor the front of a liquid plug and/or a gas plug as it is displaced.

The angle formed by the axis of the deformation measuring sensors relative to the longitudinal axis X of the tube 1 is selected by preference from within the range (+15, −15°).

The pressure sensor and the deformation measuring sensors are connected to a processing and control device such as a micro-controller 7 programmed to acquire and process data in order to determine at least one parameter associated with the multi-phase flow, such as the quantity of a liquid or gaseous phase or its density.

This latter can also be programmed to transmit command signals to the associated device control equipment (not illustrated), particularly the fluid pumping means used in the petroleum production networks, in order to regulate and optimize operation thereof.

In the case of pressurize fluids, it has proved to be of advantage to place the membrane at equi-pressure by filling the annular space 10 around the flexible membrane 2 of diameter d with a fluid such as an incompressible liquid. The flexible membrane or a part of the membrane transmits the internal pressure from the pipe 12, 13 to the incompressible fluid.

The sleeve tube has a fill-up orifice 8 closed off by a plug 9 and an air-purging orifice 8 closed of f by a plug 9'.

If the fluid contains a gas, this equi-pressure in the annular zone means that the risks of this gaseous phase migrating through the texture of the elastomer are minimized and hence any bubbling that might occur in the event of sudden decompression in the pipe.

Where electric elements such as cabling are provided in the measuring device, the incompressible fluid used in the annular space may be dielectric oil or any other type of fluid that will provide the equi-pressure capability without detriment to the elements.

Advantageously, the measuring sleeve 10 is provided with a stop 11 to restrict deformation of the membrane following a sharp variation in local density in the pipe such as the arrival of a sufficiently large liquid or gas plug or the passage of a pipe scraper.

The measuring sleeve 10 can also be provided with additional measuring means such as temperature sensors linked to the micro-controller 7. These sensors can be used to advantage to make any error corrections and improve the accuracy of measurements taken on the effluent.

Load sensors Cef are also used to measure the reactions at different points of the device, particularly at inlet and outlet points of the sleeve.

Analysis of the deformation of a flexible element relative to an original state is based on conventional mathematical equations applied to a beam resting on two supports for elastic materials and documented, for example, in the works of "Resistance of Materials" by Mr J. Courbon (Volume 1, 2nd edition—Dunod Paris 1964).

This formalism is used to determine at least one parameter representative of a multi-phase flow containing at least two phases whose densities are sufficiently different as to be discernible, for example a liquid phase and a gaseous phase.

The following are defined:
a moment of deflection M for a point load located at a distance a from a support, in the following way:

$M = Px(1-\alpha)/1$ for $x < \alpha$, $M = P\alpha(1-x)/1$ for $x > \alpha$ where x is the abscissa relative to an origin relative to the length of the pipe, l is the length of the flexible element;
the rotation ω of the flexible element due to the bending moment obtained by integrating the latter, ω(x,α)=ω$_0$(α)+(P/E1)[(x$^2$/2)(1−α)/1)] for x<α
ω(x,α)=ω$_0$(α)+(P/E1)[α(1−α)/2−α(1−α)$^2$/21)] for x>α
where E is the modulus of elasticity of the flexible element and 1 the inertia of the section of the flexible element.

the deflection "v" of the deflecting element by integrating $$v_1 = (x,\alpha) = \omega_0(\alpha)x + \frac{P}{EI}\left[\frac{X^3}{6}\left(\frac{1-\alpha}{l}\right)\right] \text{ for } x < \alpha \text{ and}$$

$$v_1 = (x,\alpha) = \omega_0(\alpha)x + \frac{P}{EI}\left[\frac{\alpha(l-x)(x-\alpha)}{2} - \frac{\alpha(l-\alpha)(l-2\alpha)}{6} + \frac{\alpha(l-x)^3}{6l}\right]$$

for x>α.

The relationships set out above are applied using a given method in relation to FIGS. 2A and 2B.

The petroleum effluent flowing in the element 12 of a transportation pipe penetrates the pipe 1 of the measuring sleeve.

FIG. 2A shows an idle position or initial position of the reference membrane, for example in the case of a pipe completely filled with a liquid of a density that is essentially the same as the density of the incompressible fluid at equi-pressure filling the cavity 10, relative to an axis Oz perpendicular to the axis of the pipe at origin O. The difference in deformation measured by changing the fluid is due to the difference in specific mass of the incompressible fluid and the effluent, or to the difference in their relative density.

An idle position can also be defined relative to a pipe filled with gas.

The references relating to the initial position of the membrane are noted on FIG. 2A by the points O and D.

Since the composition of the fluid varies over time, it may contain a gaseous phase at a given instant in the form of a gas pocket, which deforms or displaces the membrane relative to the initial position determined above because of the differences in density of the liquid and gaseous phases.

FIG. 2B shows the deformation of the membrane due to the passing of a gas plug. A variation in the shape of the membrane can be seen, represented by one or several deflection values measured with reference to the initial position of the membrane of FIG. 2A. The upwardly extending curvature is due to the Archimedes thrust exerted on the membrane by the incompressible fluid filling the cavity 10.

Figure 3:
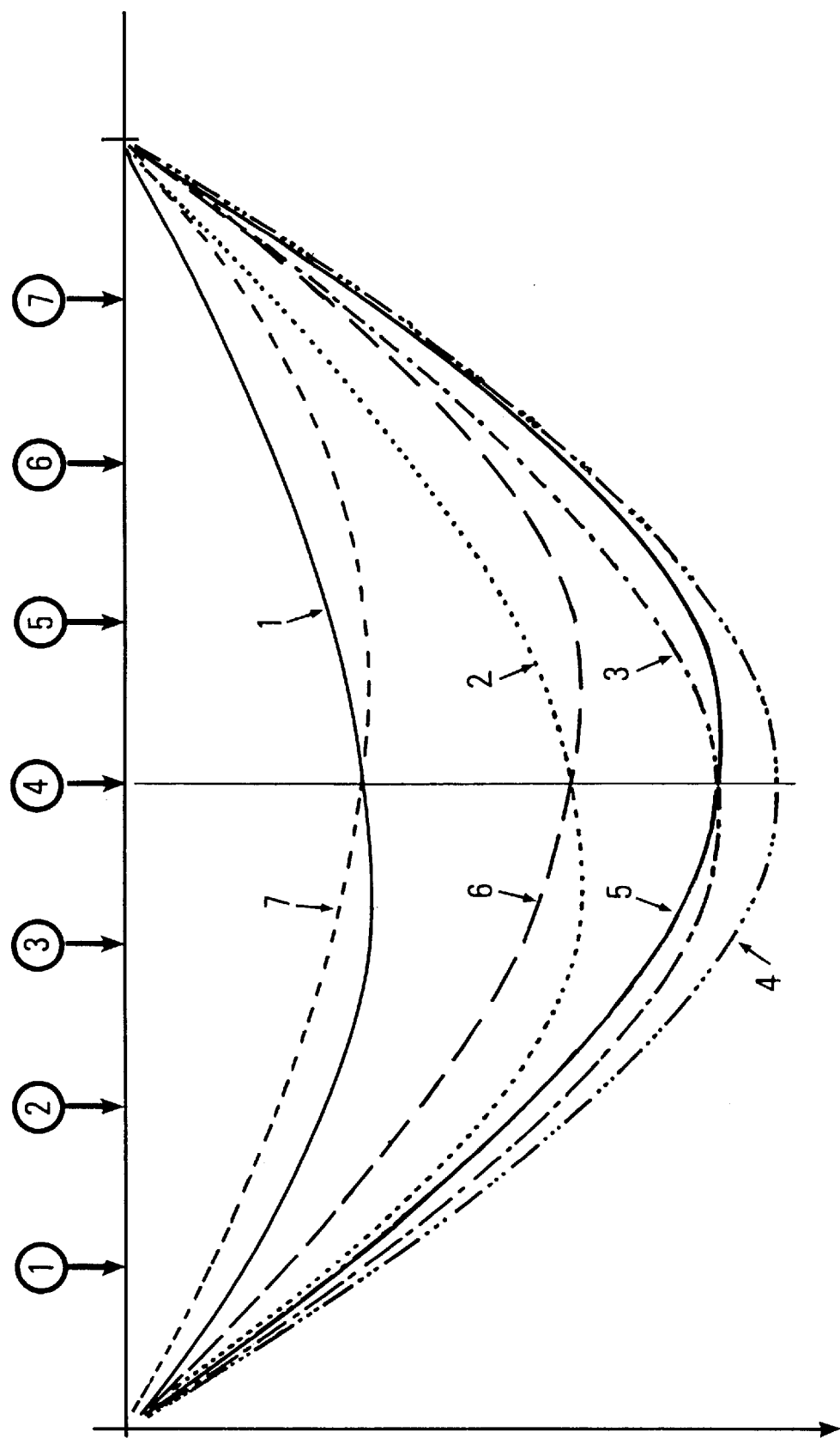
FIG. 3 is the shape assumed by a flexible element representing the distribution of loads at different instants.

The value of the deflection for a given point is located by its displacement Δz relative to the origin O or D of the axis OZ. FIG. 3 combines several possible shapes of deformation obtained using deflection measurements taken at several points along the membrane corresponding to the position sensors and shown by references 1 to 7 for a single load located to the right of one of the sensors.

The values of the measured deflections are transmitted to the micro-controller, which records for a given position xi, corresponding to a specific sensor, the value of the deflection vi. This means that each sensor produces a pair of values (vi, xi).

A pair of values can be processed in different ways, depending on the analysis being carried out and/or the parameter and/or the information required as regards the multi-phase effluent, as set out in the processing examples described below with reference to FIGS. 4A to 4F, given by way of illustration but in no respect limiting.

It is assumed that the diameter D of the pipe 1 is known and possibly the length L of the flexible element assimilated with the length over which the deflection measurements and/or effluent analysis will be conducted.

If the density of the fluid was used as a reference to determine the initial conditions, it is known, otherwise it is determined or estimated.

In a first method of implementation, the quantities of each of the phases in a fluid comprising several phases of sufficiently different densities, for example density ratios ranging between 30 and 100 for example, are determined.

The micro-controller 7 records at least two deflection values measured by the position sensors, each of the values vi being associated with a position xi, the positions xi being axially separated by a value di. Using an appropriate process, which takes account of the geometry of the pipe for example, and the basic relationships set out above, it determines the quantity Zg of the gaseous phase.

Since the value of Zg is then known as well as the geometry of the pipe, the micro-controller calculates the value of the quantity of the complementary liquid phase Zl.

By selecting another initial position as the basis, a similar reasoning can be used to determine Zl and Zg.

A calculating program can be used to estimate a curve passing between the various points plotted.

The quantity measurements of the phases will be all the more accurate if a number of sensors are used to measure deformation of the membrane. In an extreme situation, a continuous series of deflection values can be obtained representing a continuous profile of the membrane.

In another embodiment, the average density of a fluid is determined by analysing the deformation of the membrane, corresponding to the curve representing the shape which the membrane assumes along a generatrix of the membrane.

For a fluid in a state of stratified flow, the liquid and gaseous phases partially fill the substantially horizontal section of the measuring sleeve and have an essentially clearly defined horizontal interface.

The micro-controller runs through several steps, such as those set out below:
it initiates a series of measurements over several sensors distributed along the membrane,
using the values of the measured deflections, it determines a relationship between these values and/or it plots the curve representing the deformation, then
it compares this curve with a reference curve in order to assimilate the fluid with a distributed load or a point load, or it compares the values obtained and the relationship obtained with a predetermined reference relationship.

The curve and reference values are obtained using a distributed load -or a point load, for example, the loads being brought into contact with the membrane.

If the curve obtained represents a distributed flow, the micro-controller selects the value of the measured deflection for the median point and processes this datum to derive from it the average density of the fluid, for example, in the following way:
it calculates the maximum deflection Vm due to the load P distributed uniformly along the sleeve;
since the geometry of the measuring sleeve is known (taking account of the internal diameter of the sleeve) and by dividing the load P by the volume vo of the sleeve, it determines the average density of the flow ρm.

For a multi-phase fluid with phases of sufficiently different density, since the value of the density of one phase is known and using the mean density ρm, the micro-controller is able to calculate the proportion of occupancy of one or all of the phases for the section of pipe essentially corresponding to the length of the membrane.

In the case of a petroleum fluid, where the density of the liquid phase is known, this being regarded as the oil and water together due to the negligible difference in density between these two phases, the occupancy rate of the liquid phase "Zl" is derived by dividing the value of the mean density ρm by the density of the liquid phase ρl, Zl=ρm/ρl, after which the rate of occupancy of the gaseous phase Zg equal to 1−Zl=(ρl−ρm)/ρl is derived.

This processing method can be advantageously applied to fluids that can be assimilated with a uniformly distributed load, for example fluids containing quite large gas pockets, so-called dispersed fluid containing small gas bubbles or liquid droplets, or annular flows.

One example where the method set out below can be used is to process data pertaining to a fluid flow mainly consisting of a succession of liquid plugs and gas plugs.

During an initial stage, processing is based on the hypothesis that the sleeve consists solely of a liquid plug of short length so that it can be assimilated with a point load located, for example, at a distance "a" measured from the first support point A.

Figure 4A:
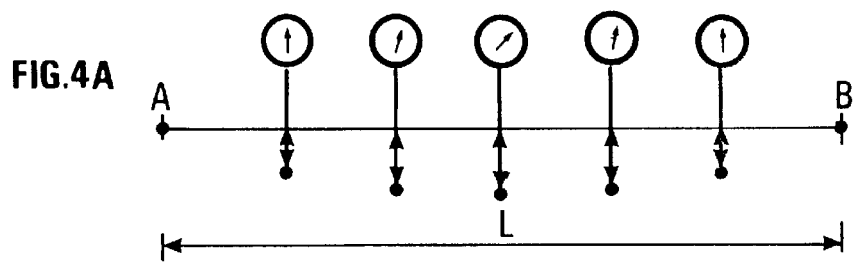
FIGS. 4A to 4E illustrate a succession of steps that might e used to implement the method.
Figure 4B:
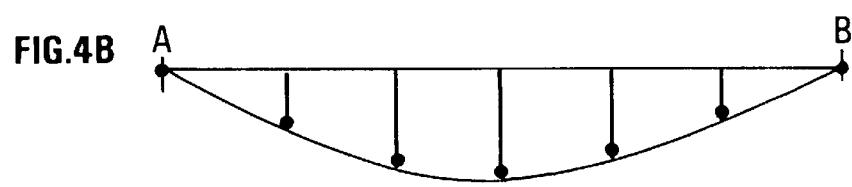

The micro-controller determines the membrane deformation curve shown in FIGS. 3 and 4A to 4B, using the deflection values measured at several points i, where i varies from 1 to n. The shape of the deformation depends on the position and distribution of the loads.

Figure 4C:
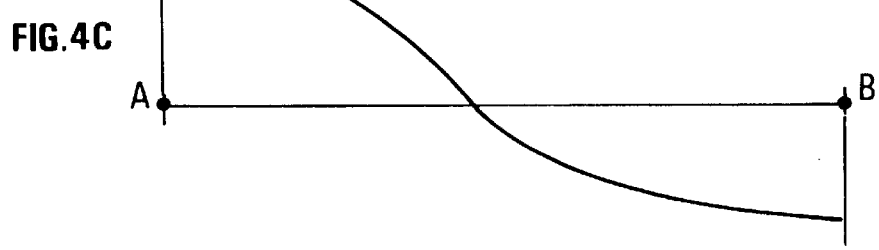

By means of a first calculation, it works out the derivative of this curve and obtains the value of the rotations represented in FIG. 4C.

Figure 4D:
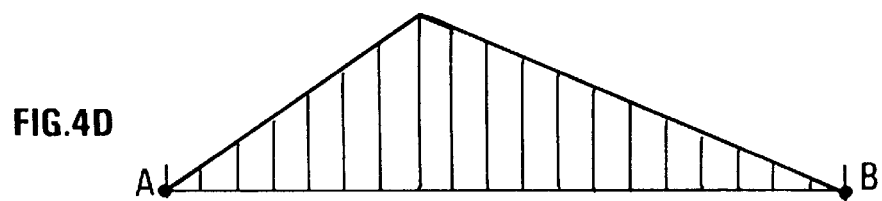

On working out the second derivative, it determines the curve of the instants of deflection or deflecting instants, shown in FIG. 4D, for a point x located on the membrane, using the following formulae:

$$\text{pour } x<\alpha M_{f_A}=R_A\chi=R_3(L-\chi)-P(a-\chi)$$

$$\text{for } x>\alpha M_{f_B}=R_B(L-\chi)=R_A\chi-P(\chi-\alpha)$$

$$x=\alpha M_{f_A}=M_{\rho_B}=R_A\alpha=R_B(L-\alpha)$$

Figure 4E:
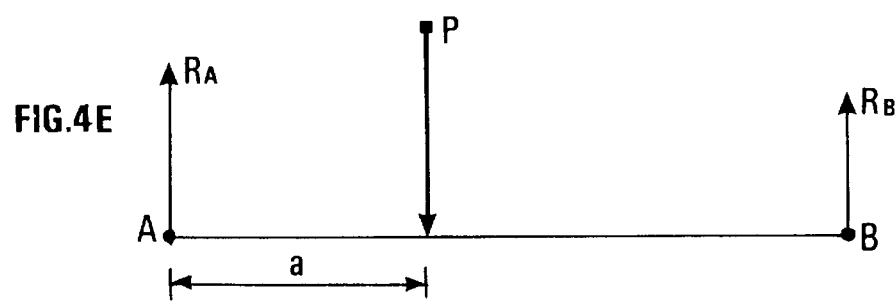

Knowing in addition that the load P=$R_A$+$R_B$, and by working out the third derivative, the micro-controller calculates the parameters given in FIG. 4E, for example
the reactions at the supports $R_A$ and $R_B$
the load P, and
the distance xp corresponding to the load position relative to the membrane.

On the basis of these data and by using a step identical to that described above in connection with a stratified flow, the micro-controller deduces the mean density or specific mass of the flow $$\rho m=P/V_0$$

and, knowing the density of the liquid, it determines the rate of occupancy of the gas $$Zg=1-(\rho m/\rho l).$$

If the fluid contains plugs of a length shorter than the length L of the membrane but nevertheless of a sufficient length for them to be assimilated with a uniformly distributed load, the third derivative is used to obtain additional information relating to the plugs, particularly their length and position or distribution.

In exactly the same way, the controller 7 determines the mean density of the fluid and the mean vacuum rate.

It can also determine the rate of aeration of plugs by comparing the mean density of the plugs with that of the pure liquids ρl.

Figure 4F:
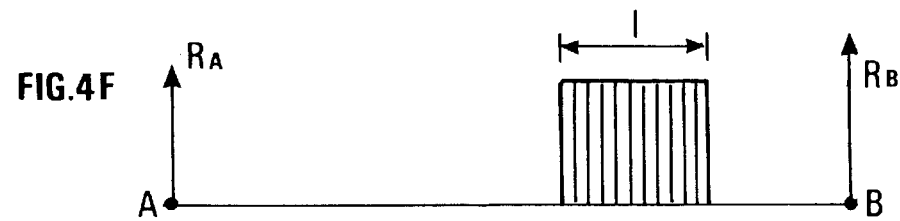

These parameters are given in FIG. 4F.

Consequently, by using the third derivative, it is possible to ascertain the structure of the fluid flow in terms of both quantity and quality, using its parameters, such as the quantity of each of the phases contained therein, the length of the plugs if there are any, and the presence of any interfaces in the case of stratified flow.

The data pertaining to the average flow rate of the fluid and/or each of the phases of a multi-phase fluid are of particular interest to producers.

The micro-controller calculates the value of the mean flow rate and/or the flow rate values of each of the phases in the following way, for example:

it takes a first series of deflection measurements at several points on the membrane in order to produce an image representing the load distribution along the membrane at an instant t1 and then a second series measured at an instant t2, it operates on the hypothesis that the length of the plug will not shorten or lengthen at the measuring instants in the vicinity of t1 and t2, it determines the location (or the image) of the load by processing the shape of the deformation curves using the analysis described (3rd derivative), since the two measuring instants t1 and t2 and the corresponding locations of the load are known, it determines the speed of the load.

From the displacement speed of the load, it calculates:

the speed of a gas plug and/or a liquid plug-of a length shorter than the length of the measuring sleeve, i.e. essentially the length of the membrane, the speed of the head and tail of a gas plug and/or a liquid plug, for a plug whose length is greater than the length of the sleeve, and, by taking an average of these two speed values, the average speed of the plug.

The micro-controller sums, for example, the different volumes associated with the liquid plugs contained in the flow circulating in the sleeve, for a given time, for example one hour, and derives therefrom the hourly flow rate of the liquid phase.

Working on the supplementary hypothesis that the gaseous and liquid phases move at essentially the same speed, the micro-controller determines the total flow rate of the multi-phase flow by multiplying the speed of the liquid phase determined previously by the transverse section of the measuring sleeve $Q_T$=S Vm.

From this, it can easily derive by subtraction the total flow rate of the gaseous phase:

$$Qg=Q_T-QL.$$

The thermodynamic parameters such as pressure and temperature can be measured and taken into account in the processing of data handled by the micro-controller.

The micro-controller can also use a thermodynamic model to make any error corrections and enhance the accuracy of the measurements.

In the case of flows that exhibit little or no discernible disruptions using the deformation analysis, the deformation measurements can not be used to determine the occupancy rate of the gaseous and liquid phases.

For this purpose, the micro-controller uses the reaction measurements RA and RB or the analysis pertaining to deformations in order to determine the vacuum rate or the quantity of gas.

Using an auxiliary speed measuring device, and by assigning a speed value measured using the auxiliary device to each of the phases, for example a conventional ultra-sound transducer, the micro-controller calculates the flow rate of the gas flow rate and/or the liquid flow rate.

Tests have shown that it was of particular significance to measure the deflection value at a preferred point 0.2*L from the first support point A, which makes it easier to distinguish between a point load and a distributed load when synthesizing the deformation.

Using another embodiment, the membrane may be of different shapes, as illustrated by way of example but not limitatively in FIGS. 5A to 5D, to suit the relevant parameters sought and the structure of the fluids being analysed.

Figure 5A:
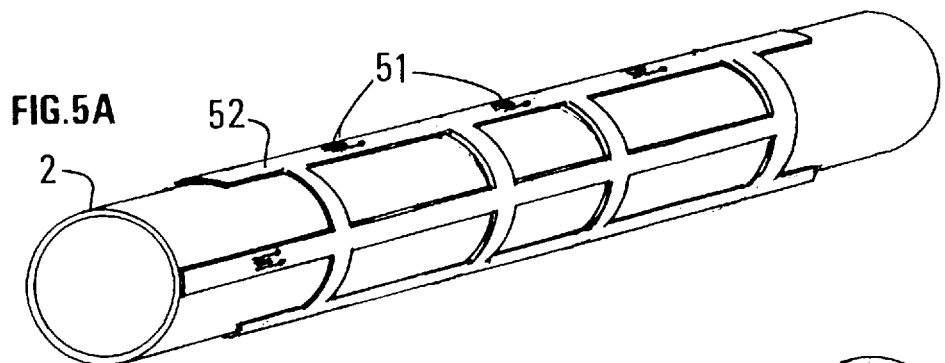
FIGS. 5A to 5D show examples of various embodiments of the membrane.

FIG. 5A illustrates an example of a flexible membrane used when the fluid in question is of the annular type and contains a gaseous phase and a liquid phase and in which the liquid film "adheres" to the wall, largely due to the high speeds of the gaseous phase. The membrane is provided with means for measuring flow friction against the wall, such as bands of bronze or beryllium. The width, thickness and number of bands is calculated, for example, by taking account of the mechanical capacity of the elastomer to behave as a semi-embedded beam at the upstream end with a simple support at the downstream end or on simple supports at both ends.

The vertical load to be considered for the measurements is theoretically subjected to Archimedes thrust. The axial load is mainly due to internal friction of the effluent against the wall, which specifically allows the friction to be measured and the flow rate values for this type of flow to be derived therefrom.

The device is provided with extensometer gauges 51, for example (known as strain gauges), arranged on metallic bands 52, for example, which may be located in the median plane and which may pick up, by means of one or several metal rings integral with the other metal bands, all or the greater part of the axial loads due to the friction. The extensometer gauges allow the bending stress and axial stress to be measured.

The various measuring means are, of course, linked to the micro-controller, which processes the various data as described above.

In another embodiment relating to the most simple case where only the instantaneous deformation is required, the measuring sleeve can be provided with metal stiffening members 53 in the form of bands or wound wires, for example, having a constant pitch of sufficient length to allow the deformation value to be measured, the said bands being located on the external wall of the elastomer or possibly embedded in the thickness of the flexible membrane.

Figure 5B:
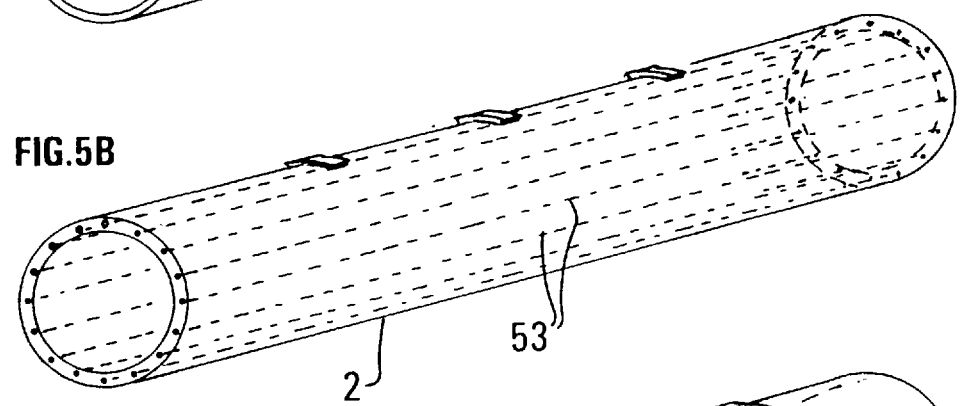
Figure 5C:
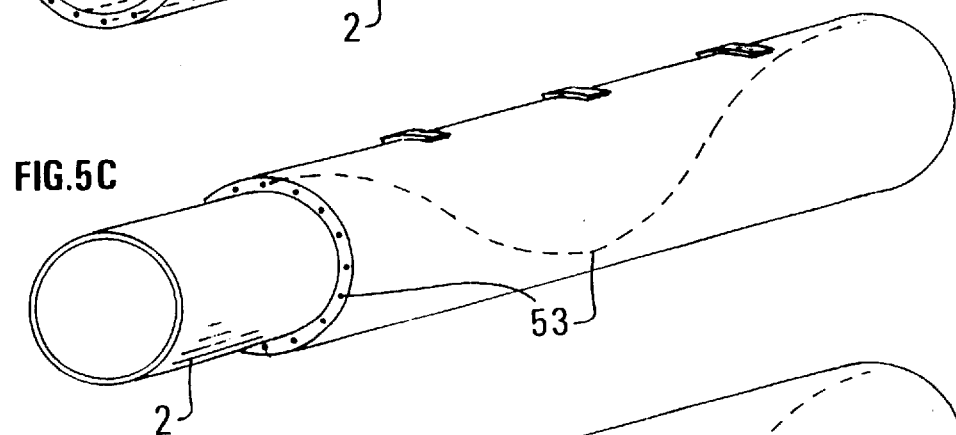
Figure 5D:
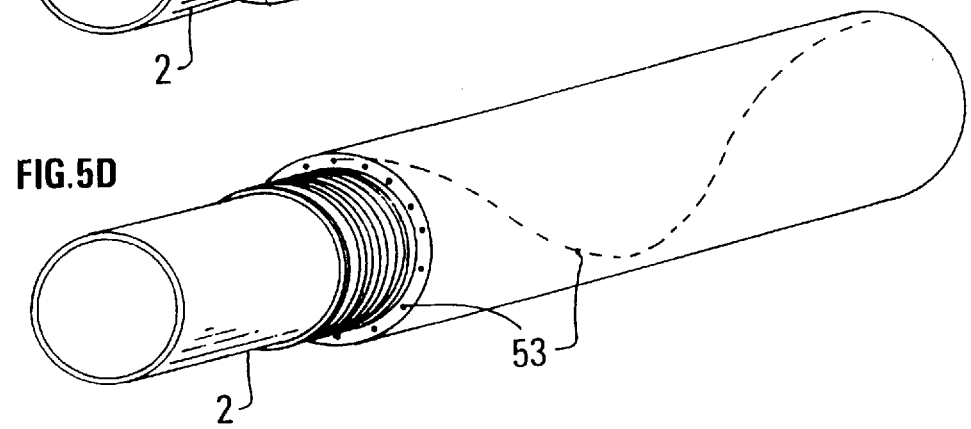

Examples of such a sleeve are shown in FIGS. 5B to 5D.

FIG. 5B illustrates a measuring sleeve provided with longitudinal stiffening wires distributed longitudinally around the sleeve, for example.

Application of the method may clearly be extended to any field involving two-phase flows in which the phases are of different densities, without departing from the scope of the invention.

The measuring sleeve described above but with a small diameter can be used to advantage on production heads and upstream of remote equipment (such as two-phase pumps, separators or any other device used in petroleum production) and possibly on large-diameter pipes, for example at the junctions of flowline networks and close to onshore or offshore processing centers.

I claim:

1. A method for determining at least one parameter associated with a fluid of variable density, where the fluid may contain one or several phases, each of which has a variable density, characterised in that the deformation value of a flexible element in contact with the fluid is measured at several points distributed over at least a portion of the length of the said flexible element, the said flexible element being placed at equi-pressure, the said flexible element being fixed to the pipe at two points at least, and these measurements are used in conjunction with a relationship linking the measurements and/or the curve passing through these various plotted measurement points, and/or the slope of the curve, to determine at least one parameter characterising the said fluid such as its average density and/or the density of each of its phases and/or the quantity of each of its phases and/or the variation in its composition.

2. A method as claimed in claim 1, characterised in that the deformation of the flexible element is measured at a point located at a distance essentially equal to 0.2*L measured relative to one of its fixing points, where L is the total length of the flexible elements.

3. A method as claimed in claim 1, characterised in that the fluid is passed through a pipe fitted with a deformable, flexible element, the speed of at least one of the phases of the fluid is determined and the deformation measurements and speed value are used to derive the average flow rate value and/or the flow rate value of each of the phases.

4. A method as claimed in claim 3, characterised in that two deformation measurements are taken on a fluid flow for two successive instants and the two measurements are correlated to derive the speed associated with at least one of the phases of the fluid.

5. A device for determining at least one parameter characteristic of a fluid with a variable density and at least one phase having different density values, the device comprising:

an enclosure with at least one internal wall;

at having at least one flexible element having a shape that matches that of at least one internal wall of the enclosure, said flexible element being fixed at two points of said at least one wall of the enclosure and positioned relative to the at least one internal wall of said enclosure so that a space is created between said internal wall and said flexible element, said flexible element forming a passage through which the fluid can flow and capable of deforming upon contact with the fluid;

an inlet for introducing at least one auxiliary, non-compressible fluid into said space, to surround said flexible element and to place said flexible element at equi-pressure, at least one sensor for measuring deformation of said flexible element when said fluid is flowing inside the element; and a processing device, linked to said sensor, for using measured values to determine said at least one parameter.

6. A device according to claim 5, wherein said enclosure is a tube and said flexible element is a membrane circular in cross-section with a diameter smaller than an internal diameter of said tube, and said space is an annular space.

7. A device according to claims 5, wherein said sensor is selected from the group consisting of a mechanical sensor, an inductive sensor, a capacitor sensor, and wherein an axis of the sensor forms an angle of between −15° to +15° with a longitudinal axis of said enclosure.

8. A device according to one of claims 5, wherein said flexible element is a membrane provided with stiffening members enabling a friction measurement to be taken.

9. A device according to one of claims 5, wherein said device is positioned essentially horizontally between two sections of a transport pipeline.

10. A device according to claim 5, wherein said flexible element is in the shape of a sleeve.

11. A method for determining the variation in structure or the quantity of at least one phase of a fluid or the flow rate of each of a phase of a multi-phase petroleum effluent including at least one liquid phase and one gaseous phase comprising:

attaching a device according to claim 5 to a fluid enclosure and using said device to determine the variation in structure or the quantity of at least one phase of a fluid or the flow rate of each of a phase of a multi-phase petroleum effluent.

12. A device according to claim 5, wherein said sensor is capable of using measured values to determine said parameter, wherein said measured values are selected from the group consisting of a variation of each fluid phase; a quantity of each phase; a speed of each phase; a structure of said fluid; a mean density of said fluid; a density of each phase; and a variation in the fluid composition.

13. A device for determining at least one parameter characteristic of a fluid with a variable density, wherein said fluid may contain one or several phases having different density values, comprising:

a tube including a flexible membrane having a shape that corresponds with the shape of said tube, wherein a space surrounds said flexible membrane and said flexible membrane is filled with an incompressible fluid which surrounds said membrane, and wherein said fluid flows inside said flexible membrane; and at least one measuring means for measuring deformation of said flexible membrane when said fluid is inside the membrane, and an appropriate processing device is linked to said measuring means and is capable of using measured values to determine said parameter.

14. A device for determining at least one parameter characteristic of a fluid with a variable density, wherein said fluid may contain one or several phases having different density values, comprising:

a circular pipe including a flexible membrane having a circular cross-section and shape that corresponds with the shape of a circular pipe, wherein the diameter of the membrane is smaller than the diameter of the pipe; wherein a space between the internal wall of the pipe and said membrane is an annular space; and at least one measuring means for measuring deformation of said flexible membrane when said fluid is flowing inside the membrane, and an appropriate processing device is linked to said measuring means and is capable of using measured values to determine said parameter.

15. A device for determining at least one parameter characteristic of a fluid with a variable density, wherein said fluid has at least one phase having different density values, comprising:

an enclosure with at least one internal wall, at least one flexible element capable of deforming when said flexible element is in contact with a fluid, said flexible element having a shape that matches that of the enclosure, wherein said flexible element is fixed at two points of said at least one wall of the enclosure, said flexible element being positioned relative to an internal wall of said enclosure to create a space between said internal wall and said flexible element; and said enclosure is provided with means for introducing at least one auxiliary, non-compressible fluid into said space to place said flexible element at equi-pressure with said non-compressible fluid surrounding the flexible membrane; and at least one measuring means for measuring deformation of said flexible element when said fluid is flowing inside the membrane, an appropriate processing device linked to said measuring means and capable of using measured values to determine said parameter; wherein said measuring means is selected from the group consisting of a mechanical sensor, an inductive sensor and a capacitor sensor, and wherein an axis of said sensor forms an angle or between −15° to +15° with a longitudinal axis of said pipe.

* * * * *